US009042612B2

(12) United States Patent
Gkanatsios et al.

(10) Patent No.: US 9,042,612 B2
(45) Date of Patent: *May 26, 2015

(54) IMAGE HANDLING AND DISPLAY IN X-RAY MAMMOGRAPHY AND TOMOSYNTHESIS

(71) Applicant: Hologic, Inc., Bedford, MA (US)

(72) Inventors: Nikolaos Gkanatsios, Danbury, CT (US); Loren Niklason, Hillsborough, NC (US); Ian Shaw, Yorktown Heights, NY (US); Christopher Ruth, Danvers, MA (US); Andrew P. Smith, Lexington, MA (US); Jay A. Stein, Boston, MA (US)

(73) Assignee: Hologic, Inc., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/646,317

(22) Filed: Oct. 5, 2012

(65) Prior Publication Data

US 2013/0028374 A1 Jan. 31, 2013

Related U.S. Application Data

(63) Continuation of application No. 13/027,771, filed on Feb. 15, 2011, now Pat. No. 8,285,020, which is a continuation of application No. 12/539,460, filed on Aug. 11, 2009, now Pat. No. 7,916,915, which is a (Continued)

(51) Int. Cl.
*G06K 9/00* (2006.01)
*A61B 6/00* (2006.01)
(Continued)

(52) U.S. Cl.
CPC .............. *A61B 6/502* (2013.01); *A61B 6/025* (2013.01); *A61B 6/463* (2013.01); *A61B 6/464* (2013.01); *A61B 6/465* (2013.01); *G06T 7/0012* (2013.01); *G06T 11/006* (2013.01);
(Continued)

(58) Field of Classification Search
CPC ... G06T 7/0024; G06T 11/006; G06T 11/008; G06T 2207/30068; G06T 11/003; A61B 6/502; A61B 6/5229; A61B 6/463
USPC ........ 382/128, 131, 132; 378/23, 37, 68, 154, 378/152, 163, 165, 101
See application file for complete search history.

(56) References Cited

U.S. PATENT DOCUMENTS 3,502,878 A 3/1970 Stewart
3,863,073 A 1/1975 Wagner
(Continued)

FOREIGN PATENT DOCUMENTS

EP 0775467 A1 5/1997
EP 0982001 A1 3/2000
(Continued)

OTHER PUBLICATIONS

Heang-Ping Chan et al., "ROC study of the effect of stereoscopic imaging on assessment of breast lesions", Medical Physics, vol. 32, No. 4, Apr. 2005.

(Continued)

*Primary Examiner* — Ali Bayat

(57) ABSTRACT

A method and system for acquiring, processing, storing, and displaying x-ray mammograms Mp tomosynthesis images Tr representative of breast slices, and x-ray tomosynthesis projection images Tp taken at different angles to a breast, where the Tr images are reconstructed from Tp images.

23 Claims, 10 Drawing Sheets

Related U.S. Application Data continuation of application No. 11/827,909, filed on Jul. 13, 2007, now Pat. No. 7,616,801, which is a continuation of application No. 11/604,069, filed on Nov. 24, 2006, now abandoned, which is a continuation-in-part of application No. 11/271,050, filed on Nov. 11, 2005, now Pat. No. 7,577,282, said application No. 11/604,069 is a continuation-in-part of application No. 10/723,486, filed on Nov. 26, 2003, now Pat. No. 7,831,296, and a continuation-in-part of application No. 10/305,480, filed on Nov. 27, 2002, now Pat. No. 7,123,684.

(60) Provisional application No. 60/628,516, filed on Nov. 15, 2004, provisional application No. 60/631,296, filed on Nov. 26, 2004.

(51) Int. Cl.
*A61B 6/02* (2006.01)
*G06T 7/00* (2006.01)
*G06T 11/00* (2006.01)

(52) U.S. Cl.
CPC .. *G06T 2200/24* (2013.01); *G06T 2207/10112* (2013.01); *G06T 2207/20068* (2013.01); *G06T 2207/30068* (2013.01)

(56) References Cited

U.S. PATENT DOCUMENTS

| | | |
|---|---|---|
| 3,971,950 A | 7/1976 | Evans et al. |
| 4,160,906 A | 7/1979 | Daniels et al. |
| 4,559,641 A | 12/1985 | Caugant et al. |
| 4,744,099 A | 5/1988 | Huettenrauch et al. |
| 4,773,086 A | 9/1988 | Fujita et al. |
| 4,821,727 A | 4/1989 | Levene et al. |
| 4,969,174 A | 11/1990 | Scheid et al. |
| 4,989,227 A | 1/1991 | Tirelli et al. |
| 5,018,176 A | 5/1991 | Romeas et al. |
| RE33,634 E | 7/1991 | Yanaki |
| 5,029,193 A | 7/1991 | Saffer |
| 5,078,142 A | 1/1992 | Siczek et al. |
| 5,163,075 A | 11/1992 | Lubinsky et al. |
| 5,164,976 A | 11/1992 | Scheid et al. |
| 5,199,056 A | 3/1993 | Darrah |
| 5,240,011 A | 8/1993 | Assa |
| 5,289,520 A | 2/1994 | Pellegrino et al. |
| 5,365,562 A | 11/1994 | Toker |
| 5,415,169 A | 5/1995 | Siczek et al. |
| 5,426,685 A | 6/1995 | Pellegrino et al. |
| 5,452,367 A | 9/1995 | Bick et al. |
| 5,506,877 A | 4/1996 | Niklason et al. |
| 5,526,394 A | 6/1996 | Siczek et al. |
| 5,539,797 A | 7/1996 | Heidsieck et al. |
| 5,553,111 A | 9/1996 | Moore et al. |
| 5,592,562 A | 1/1997 | Rooks |
| 5,594,769 A | 1/1997 | Pellegrino et al. |
| 5,596,200 A | 1/1997 | Sharma et al. |
| 5,598,454 A | 1/1997 | Franetzke et al. |
| 5,609,152 A | 3/1997 | Pellegrino et al. |
| 5,627,869 A | 5/1997 | Andrew et al. |
| 5,668,889 A | 9/1997 | Hara |
| 5,719,952 A | 2/1998 | Rooks |
| 5,735,264 A | 4/1998 | Siczek et al. |
| 5,769,086 A | 6/1998 | Ritchart et al. |
| 5,803,912 A | 9/1998 | Siczek et al. |
| 5,818,898 A | 10/1998 | Tsukamoto et al. |
| 5,828,722 A | 10/1998 | Ploetz et al. |
| 5,872,828 A | 2/1999 | Niklason et al. |
| 5,878,104 A | 3/1999 | Ploetz |
| 5,896,437 A | 4/1999 | Ploetz |
| 5,986,662 A | 11/1999 | Argiro et al. |
| 6,005,907 A | 12/1999 | Ploetz |
| 6,022,325 A | 2/2000 | Siczek et al. |
| 6,075,879 A | 6/2000 | Roehrig et al. |
| 6,091,841 A | 7/2000 | Rogers et al. |
| 6,137,527 A | 10/2000 | Abdel-Malek et al. |
| 6,141,398 A | 10/2000 | He et al. |
| 6,149,301 A | 11/2000 | Kautzer et al. |
| 6,175,117 B1 | 1/2001 | Komardin et al. |
| 6,196,715 B1 | 3/2001 | Nambu et al. |
| 6,216,540 B1 | 4/2001 | Nelson et al. |
| 6,219,059 B1 | 4/2001 | Argiro |
| 6,233,473 B1 | 5/2001 | Shepherd et al. |
| 6,243,441 B1 | 6/2001 | Zur |
| 6,256,370 B1 | 7/2001 | Yavuz |
| 6,272,207 B1 | 8/2001 | Tang |
| 6,292,530 B1 | 9/2001 | Yavus et al. |
| 6,327,336 B1 | 12/2001 | Gingold et al. |
| 6,341,156 B1 | 1/2002 | Baetz et al. |
| 6,375,352 B1 | 4/2002 | Hewes et al. |
| 6,411,836 B1 | 6/2002 | Patel et al. |
| 6,415,015 B2 | 7/2002 | Nicolas et al. |
| 6,442,288 B1 | 8/2002 | Haerer et al. |
| 6,459,925 B1 | 10/2002 | Nields et al. |
| 6,556,655 B1 | 4/2003 | Chichereau et al. |
| 6,574,304 B1 | 6/2003 | Hsieh |
| 6,597,762 B1 | 7/2003 | Ferrant et al. |
| 6,611,575 B1 | 8/2003 | Alyassin et al. |
| 6,620,111 B2 | 9/2003 | Stephens et al. |
| 6,626,849 B2 | 9/2003 | Huitema et al. |
| 6,633,674 B1 | 10/2003 | Barnes et al. |
| 6,638,235 B2 | 10/2003 | Miller et al. |
| 6,647,092 B2 | 11/2003 | Eberhard et al. |
| 6,744,848 B2 | 6/2004 | Stanton et al. |
| 6,748,044 B2 | 6/2004 | Sabol et al. |
| 6,751,285 B2 * | 6/2004 | Eberhard et al. ............. 378/37 |
| 6,758,824 B1 | 7/2004 | Miller et al. |
| 6,813,334 B2 | 11/2004 | Koppe et al. |
| 6,882,700 B2 | 4/2005 | Wang et al. |
| 6,885,724 B2 | 4/2005 | Li et al. |
| 6,912,319 B1 | 6/2005 | Eberhard et al. |
| 6,940,943 B2 | 9/2005 | Claus et al. |
| 6,978,040 B2 | 12/2005 | Berestov |
| 6,999,554 B2 | 2/2006 | Mertelmeier |
| 7,110,490 B2 | 9/2006 | Eberhard et al. |
| 7,123,684 B2 | 10/2006 | Jing et al. |
| 7,127,091 B2 | 10/2006 | Op De Beek et al. |
| 7,245,694 B2 | 7/2007 | Jing et al. |
| 7,315,607 B2 | 1/2008 | Ramsauer |
| 7,319,735 B2 | 1/2008 | Defreitas et al. |
| 7,323,692 B2 | 1/2008 | Rowlands et al. |
| 7,430,272 B2 | 9/2008 | Jing et al. |
| 7,443,949 B2 | 10/2008 | Defreitas et al. |
| 7,760,924 B2 | 7/2010 | Ruth |
| 7,916,915 B2 | 3/2011 | Gkanatsios |
| 8,285,020 B2 * | 10/2012 | Gkanatsios et al. .......... 382/128 |
| 2001/0038681 A1 | 11/2001 | Stanton et al. |
| 2002/0012450 A1 | 1/2002 | Tsujii |
| 2002/0050986 A1 | 5/2002 | Inouc et al. |
| 2003/0018272 A1 | 1/2003 | Treado et al. |
| 2003/0026386 A1 | 2/2003 | Tang |
| 2003/0073895 A1 | 4/2003 | Nields et al. |
| 2003/0095624 A1 | 5/2003 | Eberhard et al. |
| 2003/0169847 A1 | 9/2003 | Karellas |
| 2003/0194050 A1 | 10/2003 | Eberhard et al. |
| 2003/0194051 A1 | 10/2003 | Wang et al. |
| 2003/0194121 A1 | 10/2003 | Eberhard et al. |
| 2003/0210254 A1 | 11/2003 | Doan et al. |
| 2003/0212327 A1 | 11/2003 | Wang |
| 2003/0215120 A1 | 11/2003 | Uppaluri et al. |
| 2004/0094167 A1 | 5/2004 | Brady et al. |
| 2004/0101095 A1 | 5/2004 | Jing et al. |
| 2004/0109529 A1 | 6/2004 | Eberhard et al. |
| 2004/0171986 A1 | 9/2004 | Tremaglio, Jr. et al. |
| 2004/0267157 A1 | 12/2004 | Miller et al. |
| 2005/0049521 A1 | 3/2005 | Miller et al. |
| 2005/0063509 A1 | 3/2005 | DeFreitas et al. |
| 2005/0078797 A1 | 4/2005 | Danielsson et al. |
| 2005/0113681 A1 | 5/2005 | DeFreitas et al. |
| 2005/0113715 A1 | 5/2005 | Schwindt et al. |
| 2005/0135555 A1 | 6/2005 | Claus et al. |

(56) References Cited

U.S. PATENT DOCUMENTS

| | | |
|---|---|---|
| 2005/0135664 A1 | 6/2005 | Kaufhold et al. |
| 2005/0226375 A1 | 10/2005 | Eberhard et al. |
| 2006/0030784 A1 | 2/2006 | Miller et al. |
| 2006/0098855 A1 | 5/2006 | Gkanatsios et al. |
| 2006/0129062 A1 | 6/2006 | Nicoson et al. |
| 2006/0155209 A1 | 7/2006 | Miller et al. |
| 2006/0291618 A1 | 12/2006 | Eberhard et al. |
| 2007/0030949 A1 | 2/2007 | Jing et al. |
| 2007/0223651 A1 | 9/2007 | Wagenaar et al. |
| 2007/0225600 A1 | 9/2007 | Weibrecht et al. |
| 2007/0242800 A1 | 10/2007 | Jing et al. |
| 2008/0019581 A1 | 1/2008 | Gkanatsios et al. |
| 2008/0045833 A1 | 2/2008 | Defreitas et al. |
| 2008/0130979 A1 | 6/2008 | Ren et al. |
| 2009/0003519 A1 | 1/2009 | Defreitas et al. |

FOREIGN PATENT DOCUMENTS

| | | |
|---|---|---|
| EP | 1428473 A2 | 6/2004 |
| JP | 2001-346786 A | 12/2001 |
| WO | WO90/05485 | 5/1990 |
| WO | WO98/16903 | 4/1998 |
| WO | WO 00/51484 | 9/2000 |
| WO | WO2005/051197 A1 | 6/2005 |
| WO | WO2005/110230 A1 | 11/2005 |
| WO | WO2005/112767 A1 | 12/2005 |
| WO | WO2006/055830 A2 | 5/2006 |
| WO | WO2006/058160 A2 | 6/2006 |

OTHER PUBLICATIONS

Federica Pediconi et al., "Color-coded automated signal intensity-curve for detection and characterization of breast lesions: Preliminary evaluation of a new software for MR-based breast imaging", International Congress Series 1281 (2005) 1081-1086.

Senographe 700 & 800T (GE); 2-page download on Jun. 22, 2006 from www.gehealthcare.com/inen/rad/whe/products/mswh800t.html.; Figures 1-7 on 4 sheets re lateral shift compression paddle.

"Filtered Back Projection," (NYGREN) published May 8, 2007; URL: http://web.archive.org/web/19991010131715/http://www.owlnet.rice.edu/~elec539/Projects97/cult/node2.html.

Kita et al., "Correspondence between different view breast X-rays using simulation of breast deformation", Proceedings 1998 IEE Computer Society Conference on Computer Vision and Pattern Recongnition, Santa Basbara, CA, Jun. 23-25, 1998, pp. 700-707.

Niklason, Loren T. et al., "Digital Tomosynthesis in Breast Imaging", Radiology, Nov. 20, 1997, vol. 205, No. 2, pp. 399-406.

Pisano, Etta D. et al., "Digital Mammography", Radiology, vol. 234, No. 2, Feb. 2005, pp. 353-362.

\* cited by examiner

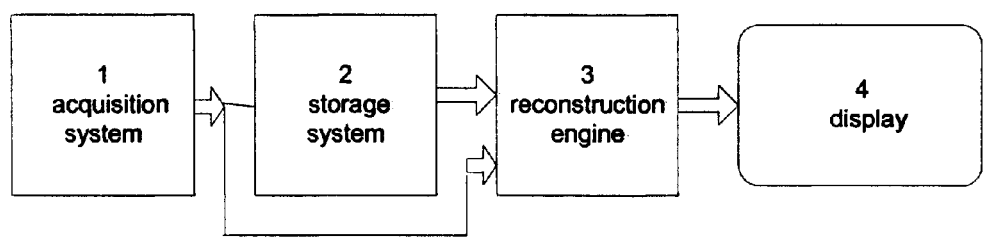
Figure 1 Flow of data through a system where the reconstructions occur after the storage system.
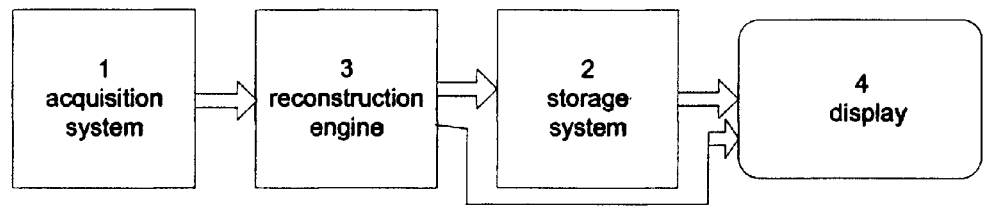
Figure 2 Flow of data through a system where the reconstructions occur before the storage system.

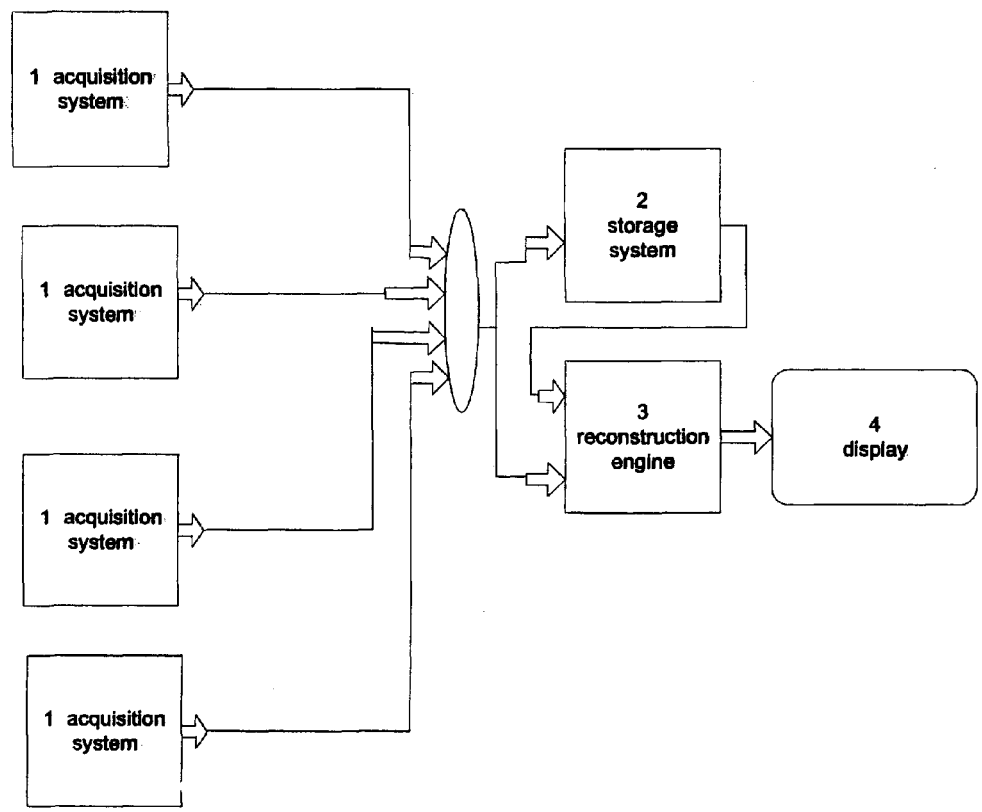
Figure 3 System arrangement for four acquisition gantries feeding a single reconstruction system

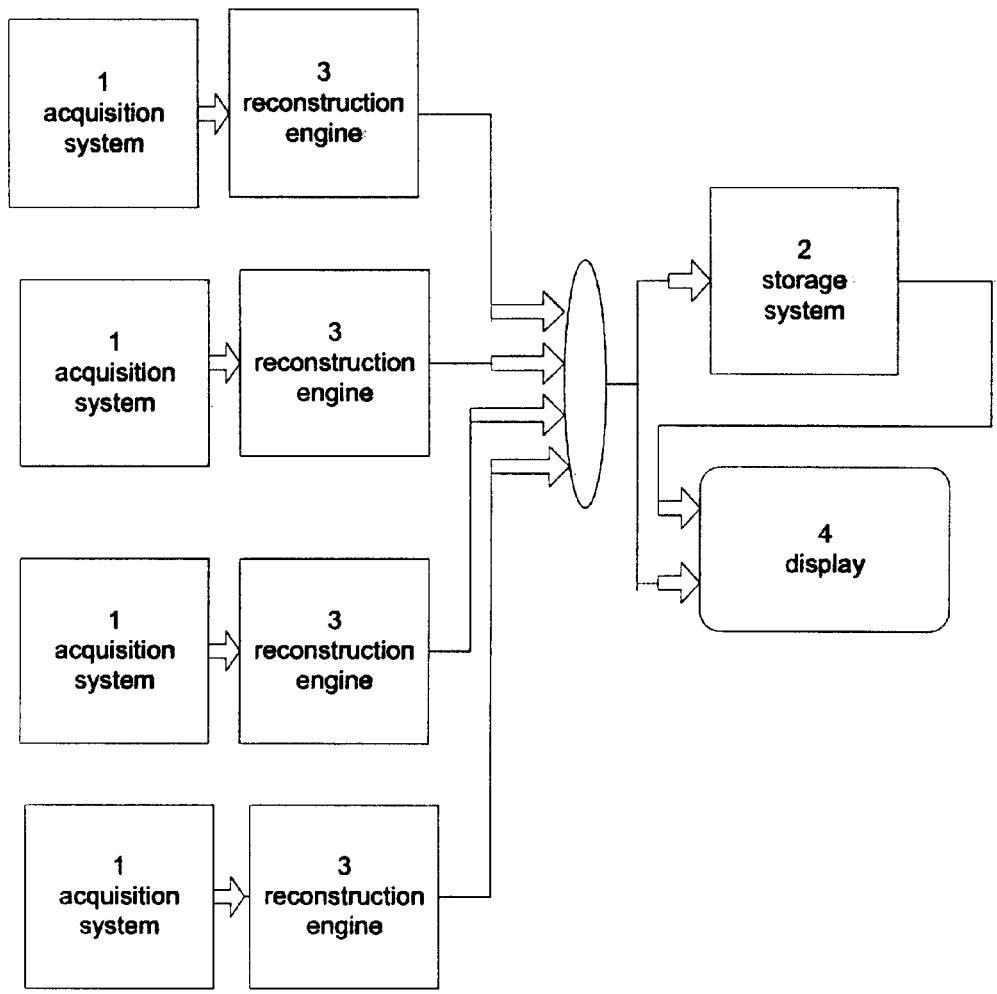
Figure 4 System arrangement for four acquisition gantries each with their own reconstruction system

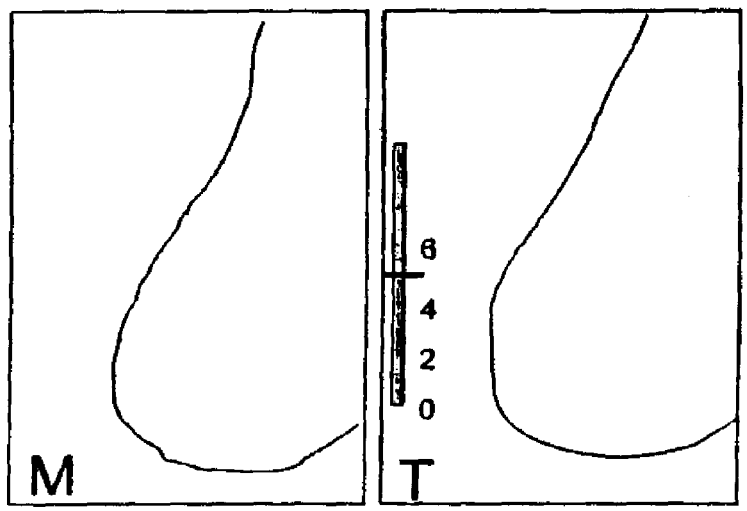
Figure 5. Display of Tomosynthesis image separate from Conventional image

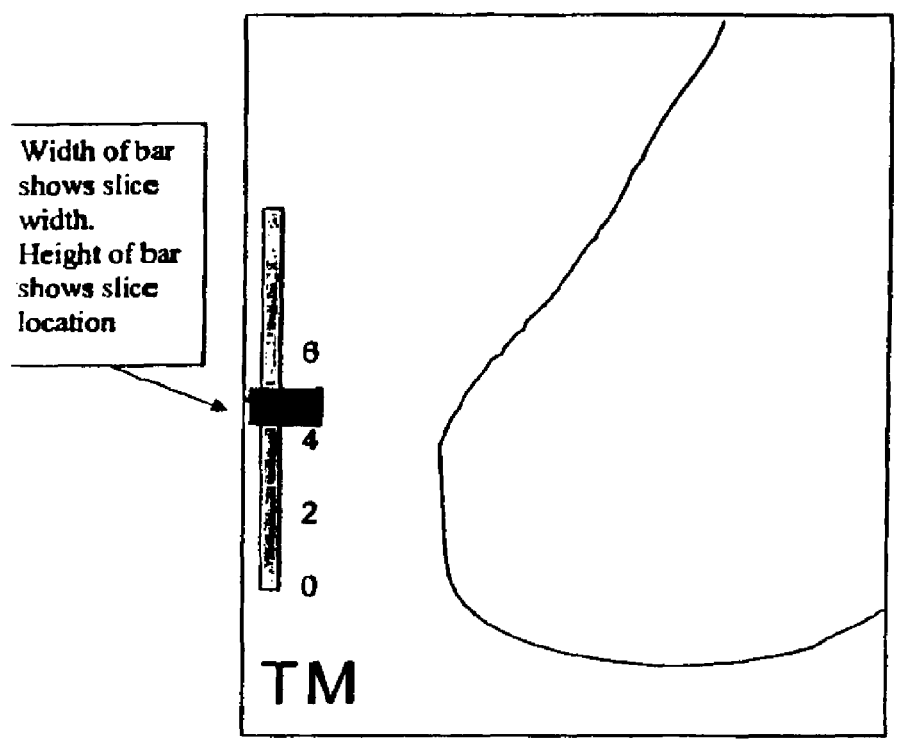
Figure 6 Display of Single View for Combination Procedure

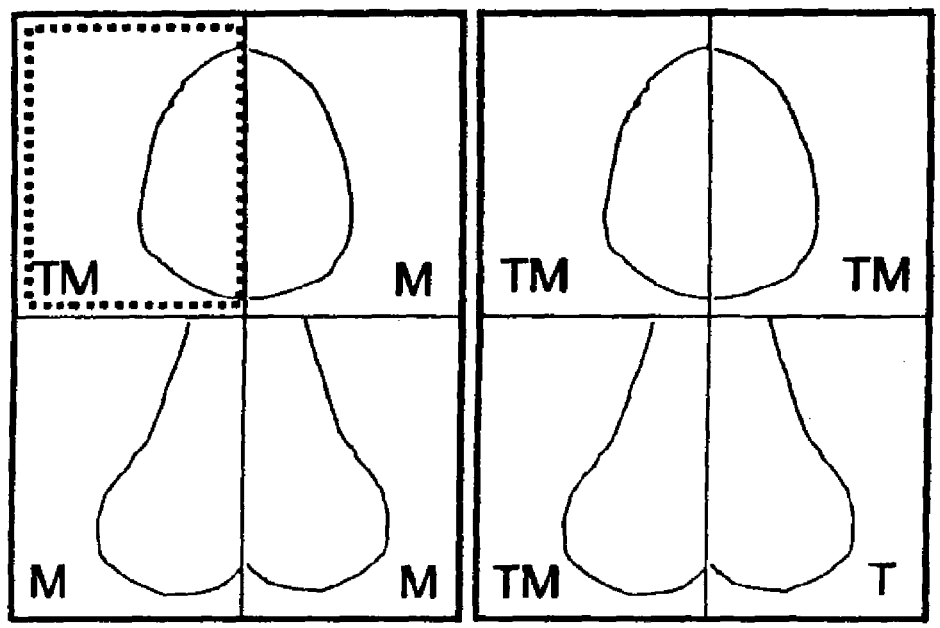
Figure 7. Display showing simultaneous review of mammograms, tomosynthesis images, and combination mammogram+tomosynthesis images

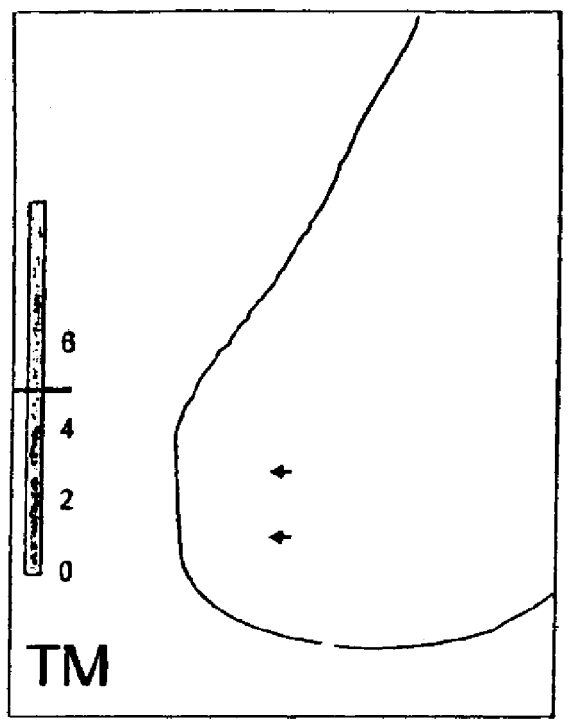
Figure 8. Display of tomosynthesis/mammogram images showing CAD mark locations, shown by arrows, at locations 1 and 3 cm

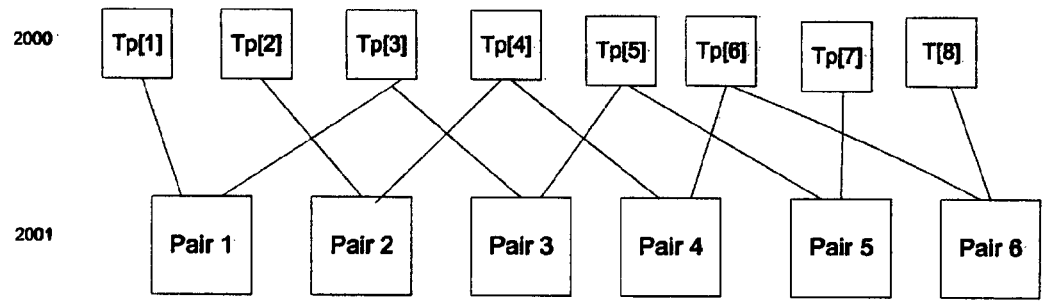
Figure 9. Six stereo pairs 2001 viewed sequentially from the eight Tp projections 2000
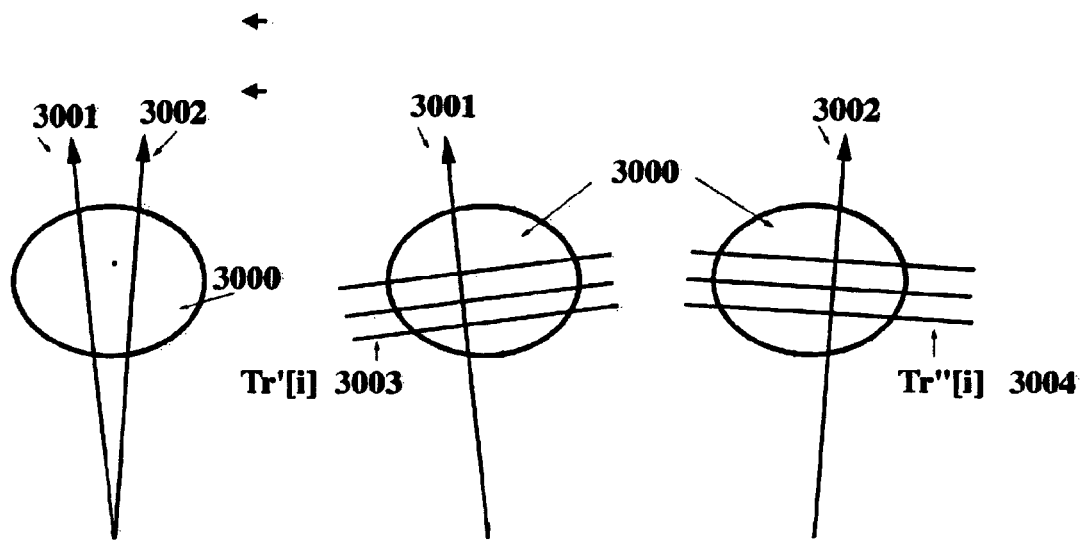
Figure 10. Stereo pairs Tr'[i] and Tr''[i] (3003 and 3004) derived from reconstructions of object 3000 from two differing angles 3001 and 3002.

IMAGE HANDLING AND DISPLAY IN X-RAY MAMMOGRAPHY AND TOMOSYNTHESIS

CROSS-REFERENCE TO RELATED APPLICATIONS

This application is a continuation of U.S. application Ser. No. 13/027,771, fled Feb. 15 2011, which in turn is a continuation of U.S. application Ser. No. 12/539,460, filed Aug. 11, 2009, which in turn is a continuation of U.S. application Ser. No. 11/827,909, filed Jul. 13, 2007 (now U.S. Pat. No. 7,616, 801) which in turn is a continuation of U.S application Ser. No. 11/604,069, filed Nov. 24, 2006, now abandoned, which in turn is (i) a continuation-in-part U.S application Ser. No. 11/271,050, filed Nov. 10, 2005 (now U.S Pat. No. 7,577,282) which claims the benefit of provisional application No. 60/628,516 filed Nov. 15, 2004 and provisional application No. 60/631,296 filed Nov. 26, 2004, (ii) a continuation-in-part of U.S. application Ser. No. 10/723,486 filed Nov. 26, 2003, (now U.S. Pat. No. 7,831,296) and (iii) a continuation-in-part of U.S. application Ser. No. 10/305,480, tiled Nov. 27, 2002 (now U.S. Pat. No. 7,123,684), and incorporates herein by reference the entire contents of each of said earlier-filed patent applications.

FIELD

This patent specification pertains to x-ray mammography and tomosynthesis, and more specifically to techniques and equipment for acquiring, processing, storing and displaying mammograms, tomosynthesis projection images, and tomosynthesis reconstructed images, and to medical image softcopy reading systems, to hanging protocols and to other medical image display features.

BACKGROUND AND SUMMARY

Mammography has long been used to screen for breast cancer and other abnormalities and for diagnostics. Traditionally, mammograms were formed on X-ray film, but more recently flat panel digital imagers have been introduced that acquire a mammogram in digital form and thereby facilitate analysis and storage and provide other benefits as well. Further, X-ray tomosynthesis of the breast has been proposed recently, as discussed in the earlier-filed applications identified above, and clinical testing has been carried out. The assignee of this patent specification, Hologic, Inc., has demonstrated at trade shows in this country a fused, multimode mammography/tomosynthesis system that takes either or both types of images, and either while the breast remains immobilized or in different compressions of the breast. Dedicated breast tomosynthesis systems also have been proposed.

Tomosynthesis as used in the systems and methods disclosed in this patent specification typically involves acquiring a plurality of tomosynthesis projection images Tp at respective angles relative to the breast, and reconstructing therefrom a plurality of tomosynthesis reconstructed images Tr representative of breast slices that have selective thicknesses. Proper display techniques are desirable to make the presentation of Tp and/or Tr images (collectively referred to here as T images) more effective and efficient for review by health professionals. When tomosynthesis projection images Tp are acquired along with conventional 2D mammograms Mp, improved display methods are desirable that facilitate the display of both T and Mp images. Effective display approaches also are desirable when tomosynthesis images Tp and/or Tr that are acquired at one time need to be compared to mammograms Mp and/or to tomosynthesis images Tp and/or Tr acquired at a different time. Effective displays also are desirable when only Tr and/or Tp images are being displayed. Another display issue relates to Computer Aided Detection (CAD) methods that use computer analysis of images to identify locations and possibly other characteristics of suspected abnormalities. CAD marks currently are placed on or are otherwise associated with mammogram images Mp, but it may be useful to place them at the appropriate location on Tr and/or Tp images o to otherwise associate them with Tr/Tp images. Conversely, it may be desirable to obtain CAD marks by processing Tp and/or Tr images, and place them at appropriate locations on Mp images. Here the notation Mp refers to a conventional mammogram, which is a two-dimensional projection image of a breast; the term Mp encompasses both a digital image as acquired by a flat panel detector or another imaging device and the image after conventional processing to prepare it for display to a health professional or for storage, e.g. in the PACS system of a hospital or another institution. Tp refers to an image that is similarly two-dimensional but is taken at a respective tomosynthesis angle between the breast and the origin of the imaging X-rays (typically the focal spot of an X-ray tube), and also encompasses the image as acquired as well as the image after being processed for display or for some other use. Tr refers to an image that is reconstructed from images Tp, for example in the manner described in said earlier-filed patent applications, and represents a slice of the breast as it would appear in a projection X-ray image of that slice at any desired angle, not only at an angle used for Tp or Mp images. The terms Tp, Tr and Mp also encompasses information, in whatever form, that is sufficient to describe such an image for display, further processing, or storage. The images Mp, Tp and Tr typically are in digital form before being displayed, and are defined by information identifying properties of each pixel in a two-dimensional array of pixels. The pixel values typically relate to respective measured or estimated or computed responses to X-rays of corresponding volumes in the breast (voxels or columns of tissue).

Yet another issue concerns the large storage requirements of tomosynthesis images Tp and/or Tr. Because the reconstructed datasets for Tr images are large, it may be better in some circumstances to store unreconstructed projections images Tp, which require less storage. Transmission times to the storage device, and from the storage device to the display workstation, can thus be reduced. The Tp images in this case can be reconstructed to Tr images just prior to viewing that requires a display of Tr images. Further, it may be desirable that images viewed on a workstation are the same or at least comparable to images viewed on a different workstation, or the same or at least comparable to previously viewed images of the same dataset, even if the software and/or hardware of the workstation or acquisition system or intermediate storage or processing systems, have changed.

Yet another issue concerns the processing time required to reconstruct tomosynthesis images Tr. Because of relatively long reconstruction times, one possible approach is to perform reconstructions at an acquisition console, and send the already-reconstructed images to display workstations. This can allow a greater reading throughput if there are several acquisition systems that are all pushing images to one or more display workstations. The system can be designed so that it can handle M acquisition consoles sending their images to all N display workstations.

In one non-limiting example disclosed in this patent specification, acquisition and display of x-ray images starts with acquiring x-ray mammography image data representative of projection mammography images Mp of patients' breasts and x-ray tomosynthesis image data representative of projection images Tp taken at different angles of at least a source of imaging x-rays relative to the patients' breasts (e.g., different angles of the focal spot in an X-ray tube relative to an immobilized breast). This acquisition can be performed by a single unit, using a single X-ray tube and a single flat panel digital imager or some other imaging device, configured to selectively acquire one or both of the mammography and tomosynthesis image data, in the same compression of a patient's breast or in different compressions, and at the same imaging session or at different times. The disclosed system and method use at least a subset of the acquired Tp images to form reconstructed tomosynthesis images Tr representative of slices of the breasts that have selected orientations and thicknesses. The system and method display at least a selected subcombination of the Mp, Tr and Tp images, preferably for concurrent viewing or at least for viewing in a single session, and preferably but not necessarily while showing, at or near the displayed images, respective labeling symbols identifying them as Mp, Tr or Tp images and possible other information that facilitates detection/diagnosis of abnormalities, such as information indicative of the position and orientation of the slices represented by Tr images, the thicknesses of such slices, etc. The information can be in alphanumeric or non-numeric form such as in the form of graphics and/or icons.

The method and system can further generate or otherwise obtain computer aided detection (CAD) marks for suspected abnormalities in said Mp images, and can display said marks at corresponding locations on or in association with Tr and/or Tp images that are related, e.g. by orientation or otherwise, with respective Mp images. In addition to location information, the CAD marks can provide information regarding, for example, the type of suspected abnormality and/or a confidence level that a mark points to an actual abnormality. CAD marks that are initially generated from or are otherwise related to some of the Tr, Tp or Mp images can be displayed at or in association with images from which they were not generated or with which they were not initially associated, at corresponding or at least related locations. Tp images can be stored together with version information indicative of at least one of an acquisition configuration used to acquire them and a reconstruction configuration used to reconstruct Tr images from said Tp images, to thereby enable later reconstruction of Tr images that match those reconstructed at an earlier time. Alternatively, or in addition, Tp images can be stored together with version information related to when they were acquired and can be later reconstructed into Tr images using a reconstruction configuration that matches the version information. A reconstruction configuration can be provided that has at least two different versions of reconstruction software, so that Tr images can be reconstructed using a version of the reconstruction software that matches the version information of the Tp images or earlier Tr images. Tr images can be reconstructed from only a subset of the acquired Tp images, which in an extreme case means reconstruction from a single Tp image to yield a Tr image that is equivalent of the Tp image. Tr images representative of at least two breast slices that differ in thickness can be formed, for example using MIP (Maximum Intensity Projection) methods or a summing method that may or may not use different weighting of the summed pixel data. The display can be toggled between Tr images representative of breast slices having different thicknesses, wherein the slices may or may not overlap in space. Through computer-processing, the volume of a lesion can be computed and displayed from information contained in the Mp, Tr and/or Tp images. The display can show concurrently, for example, Tr images reconstructed from a current acquisition of Tp images and at least one Mp image obtained from a previous acquisition involving a different breast compression. The concurrent display can be on the same or different display monitors, and can include at least Mp and/or Tr images, or at least Mp and/or Tp, images, or at least Tr and/or Tp images, or all three types of images, and can instead or additionally include 3D images formed from some or all of the acquired X-ray data, image data and/or from Mp, Tr and/or Tp images. Information indicative of status of loading Tr images for display can be shown as a part of the display. Different images can be displayed at different pixel sizes or fields of view or, alternatively, they can be selectively equalized by pixel size or field of view by selected types of interpolation or extrapolation, for example by up-converting to a smaller pixel size and thus a higher converted pixel count or by down-converting to a larger pixel size and thus a lower pixel count.

The display of Mp and T images such as Tr images can include displaying non-numeric indications of various properties of the displayed images. Such non-numeric indications can include indications of respective levels, spacing and slice thickness for displayed Tr images relative to a compressed breast imaged in an Mp image or relative to some other frame of reference, for example in the form of cross-lines on a bar related to the breast as displayed as an Mp image, wherein the height of the bar may relate to the thickness of the compressed breast, and/or non-numeric indications of respective thicknesses of breast slices represented by displayed Tr images, for example in the form of cross-bars of respective thickness on a bar related to Mp images, and/or non-numeric indications of the inclination angle of the slice or slices represented by one or more Tr images relative to a selected frame of reference such as the compressed breast that was imaged to generate the data from which the Tr images were reconstructed, and/or non-numeric indications of other parameters. Instead, or in addition to such non-numeric indications, numerical indications can be provided and displayed of the position of a slice image Tr relative to, e.g., a breast imaged in an image Mp, the thickness of the slice represented in a Tr image, and/or the orientation of that slice. Mp and T images such as Tr images can be shown overlaid on each other, and toggling can be allowed to switch between the image that is visible at the time and an image that is not, i.e. toggling between the 2D Mp image and the 3D Tr image or images. Similar toggling is available between different types of T images, of between different T images of the same type. In addition, other image display effects can be provided, such as, without limitation, fade-in/fade-out and blending two or more images at respective weightings, image overlays and masking, or other effeces, as commonly used in post-production of television images and in known image processing software such as Photoshop from Adobe.

T images such as Tr and/or Tp images can be displayed in cine mode, with selective control over the speed of changing from one image to another, the order of images for display relative to an order in which they were reconstructed or acquired, the selection of the first and last images in the cine sequence, and/or other parameters. For example, at least two sets of Tr images, each set reconstructed from different acquisitions of Tp images, can be shown concurrently and scrolled through and/or displayed in cine mode in synchronism. For example, the two sets of Tr images can be synchronized such that the first and last slice images of each set can appear on the display at the same time, which may be implemented in different ways, such as by making the number of images the same (but possibly representing slices of one thickness in one set and slices of a different thickness in the other set), or by scrolling through images of one set faster than through images of the other set, or in some other way. Making the number of Tr images of one set match that of the other set may involve interpolating images of new slices to either reduce the number of images/slices in one set or increase it. The images in that case in one set of Tr images can be made to represent slices that are all the same thickness or slices that include some that are thicker or thinner than other slices.

Tr images can be displayed in scroll or cine mode in different orders, such as by starting with the image representing the bottom of the breast (the breast side resting on a breast platform during imaging) toward to image representing the top of the breast (the breast side compressed by a compression paddle), or in reverse order, or by starting with a Tr image representing a selected intermediate slice and proceeding toward the top or the bottom of the breast, or in some other desired order. The initial image that is displayed can be the bottom image, the top image, or a selected intermediate image. In a scroll or cine mode, the display can show every image of a Tr set for a breast, or a selected subset, such as every other image or some other subset of all Tr images representing a breast. The display system can have a default mode for a new user in which it starts the scroll or cine display with the bottom image, but with provisions for this default to be changed to another display protocol for that user in which the starting image is another one of the Tr images. A selection of initial or default display modes can be provided relating to the order, speed, slice thickness and/or other parameters of display of images, and user selection among those modes can be allowed. Similar procedures are available in the case when the orientation of the Tr slices is not the same as that of the Mp or Tp slices.

Thus, information regarding image data acquisition, storage, reconstruction and/or other parameters can be selectively displayed. For example, Tr images can be identified on the display as such, thus providing an image type indication display, and additional identification can be displayed in association with a displayed image that identifies the position in the breast of the slice represented by the displayed Tr image, the thickness of the slice, the orientation of the slice, and/or some other property associated with the displayed Tr image. Corresponding or at least similar display of information can be associated with different types of displayed images, such as Tp and Mp images and displayed in association with the display of the images. In the alternative, images such as Tr, Tp, and/or Mp can be displayed in different combinations and/or sub-combinations that may include the same type of images displayed concurrently or toggled, or different types of images displayed concurrently or toggled, without providing some or any of the identifications discussed above. Tr images can be printed in an N×M format (where N and M are positive integers), and printing of any images displayed on one or more monitors in WISIWIG format can be provided.

Compression of Mp, Tp, and/or Tr images and/or of other image data can be selectively carried out prior to storing or archiving the images. The compression can be lossless, or it can be lossy to a selected degree. Reconstruction of Tr images can be selectively carried out from compressed Tp images, preferable after suitable decompression. Window/level controls can be provided for at least selected ones of the displayed Tr images, and the controls can be set by the user, or automatically, to control the window width and/or the window level of only one, or only selected ones, or all of the displayed images. Image regions can be magnified for display, and the window/level controls automatically applied to the magnified regions. The Tr, dr the Tp, or both the Tr and Tp images, can be stored in PACS storage, and can be associated with related Mp images and/or with selected CAD information. The Tp images can be acquired by using coarser binning, e.g. in a direction of relative motion between the source of imaging x-rays and a breast during image acquisition, or in both directions. Alternatively, such binning can be done after the Tp images are acquired, to thereby reduce storage and further processing requirements. The Mp, Tr, and/or Tp images that are concurrently displayed can be based on image data acquired from the same breast of a patient while the breast remains immobilized under compression that can remain the same or change between the acquisition of Mp images and Tp images. Alternatively, the Mp and Tp images can come from different acquisitions at different times or different breast compressions. Image data for Tp images acquired at two or more acquisition units can be supplied to and reconstructed into Tr images at a single reconstruction unit, from which one or more data display units can acquire Tr, Tp, and/or Mp images for display, or image data for Tp images can be stored as such and only reconstructed into Tr images immediately prior to display thereof. Images with difference characteristics such as pixel size, brightness, gamma curves, etc. can be processed to make selected ones of their characteristics sufficiently similar to facilitate comparison.

An additional or alternative display approach uses the Tp and/or Tr images in stereoscopic display. For example, when any two Tp images taken at different angles to the breast are displayed concurrently and viewed such that each is seen by a different eye of the observer, depth information is visualized. Similarly, when any two Tr images are reconstructed such that their image planes are at an angle to each other, depth information can also be perceived.

Images of different types and from different sources can be displayed in desirable size and resolution. For example, an image can be displayed in (1) Fit To View Port mode, in which the size of the displayed image size is maximized such that the entire imaged breast tissue is visible, (2) True Size mode, in which a display pixel on the screen corresponds to a pixel of the image, or (3) Right Size mode, in which the size of a displayed image is adjusted so that it matches that of another image that is concurrently displayed or with which the displayed image is or can be toggled. For example, if two images of the same breast are taken and are not the same size or do not have the same special resolution, provisions are made to selectively zoom in or zoom out one of them, or zoom both, such that they appear to be the same size on the screen when they are concurrently displayed or the user toggles between them, to facilitate comparison or to otherwise facilitate detection/diagnosis. Known interpolation/extrapolation and weighting techniques can be used in such re-sizing, and known image processing technology can be used to make other characteristics of the displayed images similar in a way that facilitates detection/diagnosis.

Selected hanging protocols are provided that are unique to the different types of images with which the disclosed system deals. As one example, the hanging protocols for 2D images (e.g. Mp images) and 3D images (e.g. Tr images) are linked so that when one type of image is displayed for a given breast the other type is displayed as well. For example, when the Mp image of a breast is displayed, a tile of the Tr images and/or of the Tp images is automatically displayed at the same time, with a desired hanging protocol that may involve scrolling or cine mode presentation, or may require user input so select a particular subset of the Tr and/or Tp images or a particular individual Tr/Tp image. Thus, a combined hanging protocol set can be provided for 2D and 3D images that are concurrently displayed or toggled such that only one type is displayed at one time. In addition, the combined hanging protocol can include provisions for linked display of CAD information associated with one or both of the 2D and 3D images involved in the hanging protocol. Alternatively, the hanging protocols for 2D images are made different from those for 3D images.

When CAD information is available that is associated with any of the images that can be displayed, linking can be provided such that CAD information derived from one of the types of displayed images can be automatically associated with corresponding locations on another displayed image. For example, if CAD information has been derived on the basis of an Mp image and the Mp image is displayed at the same time as, or is toggled with, Tr images, provisions are made to selectively display CAD information associated with the appropriate locations on Tr images. Alternatively, if CAD information is derived on the basis of Tr and/or Tp images, it can be automatically selectively displayed in association with an Mp image that is displayed at the same time or is toggled with the Tr/Tp images. In one example, an Mp image with CAD marks thereon remain displayed on the screen while Tr images of the same breast are scrolled or shown in cine mode on the screen, to facilitate identification and/or assessment of suspected abnormalities in the Tr images.

When Tr images are displayed, provisions are made to selectively adjust the thickness of the slice represented by any displayed Tr image. For example, if it is desired to display a Tr image of a slice (slab) of breast tissue that is 1 cm thick but the available Tr images represent 1 mm thick slices, 10 of those Tr images can be combined into a single new Tr image that represents the 1 cm slice, using for example a known MIP (maximum intensity projection) technique.

For storage, transmission to remote locations, and/or other purposes, the images can be formatted consistent with DICOM standards. For example, each raw or displayed projection image set or reconstructed slice image set for a single view is stored as a single Secondary Capture image instance according to DICOM. The image pixel data can be encoded in a selected compressed format (CODEC) that includes all projection or slice images

BRIEF DESCRIPTION OF DRAWINGS

FIG. 1 is a block diagram illustrating flow of data through a system where reconstruction of tomosynthesis slice images Tr occurs after (or, alternatively, before) storage of acquired tomosynthesis projection images Tp.

FIG. 2 is a block diagram illustrating flow of data where the reconstruction of images Tr occurs before storage.

FIG. 3 illustrates an example where four units acquiring Tp images feed a single unit that reconstructs Tr images.

FIG. 4 illustrates an example where each of four units acquiring Tp images has its own unit for reconstructing Tr images.

FIG. 5 illustrates an example of displaying Tr (or Tp) images and mammogram images Mp at separate areas of a single screen or on different screens.

FIG. 6 illustrates an example where an Mp image and a Tr image may be shown at the same or substantially same area on a screen, with an example of a non-numeric indication of a thickness and position in the breast of a breast slice represented by a Tr image.

FIG. 7 illustrates a concurrent display of Tr and Mp images, at separate areas on a screen or as combined images.

FIG. 8 illustrates a display of Mp/Tr images with CAD marks and a non-numeric indication of Tr images in which CAD marks exist.

FIG. 9 illustrates stereoscopic display of Tp images.

FIG. 10 illustrates stereoscopic display of Tr images.

DETAILED DESCRIPTION OF PREFERRED EMBODIMENTS

Figure 11:
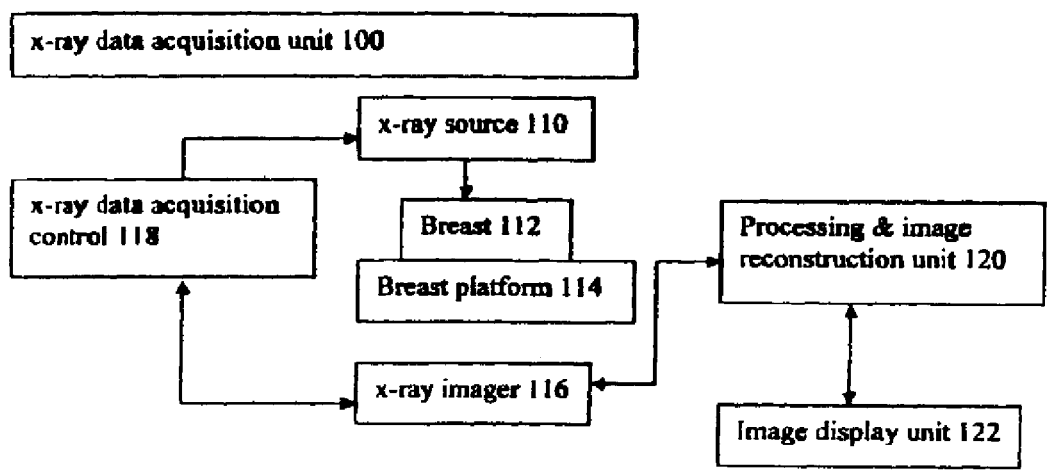
FIG. 11 is a block diagram illustrating major elements of a mammography/tomosynthesis system.

In describing preferred embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

FIG. 1 illustrates flow of data in one example of a system disclosed in this patent specification. An image data acquisition system 1 acquires tomosynthesis and/or mammography image data for Tp and/or Mp images of patients' breasts, and can take the form of and use the acquisition methods of any of the systems disclosed in said earlier-filed patent applications. Following acquisition, the data describing projection images Tp are sent to storage device 2, which can include a Picture Archiving and Communication System (PACS) storage, for example of the type commonly used in hospitals and other healthcare facilities, preferably a DICOM-compliant PACS. When images are needed for display 4, the data for Mp and/or Tp images are sent, from either acquisition system 1 or from storage device 2, to a computer system 3 configured as a reconstruction engine that can perform tomosynthesis reconstruction into images Tr representing breast slices of selected thickness and at selected orientations, as disclosed in said earlier-filed patent applications. The reconstructed slice images Tr are then sent to a display system 4 so that they can be viewed. If the reconstruction engine 3 is connected to display 4 via a fast link, then large datasets can be transmitted quickly.

Over time, there will likely be improvements to the acquisition systems and to the display systems, which may result in hardware and software upgrades and changes to reconstruction algorithms. This can create issues in viewing images taken previously. It may be important to be able to recall from storage and reconstruct an image that looks identical (or is at least comparable) to the way it looked when it was reconstructed and displayed in the past, or vice versa. Consider the example where an improvement in reconstruction algorithms improves image quality so as to allow detection of a cancerous lesion in an image where it was not visible using a previous version of the reconstruction algorithm and the then existing standard of care. While it could be useful to see older images processed with the newer algorithms, it may also be important to allow the re-display of images as they were viewed during an original detection/diagnosis. One way to accomplish this in accordance with the disclosure in this patent specification is to put a version number or some other information in the data for Tp images, which identifies the software and/or hardware versions of the Tp image data acquisition and/or Tr image reconstruction system at the time of acquisition, or to otherwise associate such information with the Tp images. During reconstruction at a later time, the reconstruction engine reads this version number or other similar information and reconstructs using the appropriate algorithm. Thus, system upgrades can maintain a library of older algorithms and/or hardware so as to be able to reconstruct using the proper technique.

An alternative design is illustrated in FIG. 2. In this example, the reconstructions at unit 3 occur near or at the acquisition station 1, and it is the reconstructions Tr that are sent to storage system 2 and display devices 4. One advantage of the configuration of FIG. 2 is in the way it handles acquisition upgrades—if a new hardware/software version has a modified reconstruction algorithm, then all Tr images reconstructed from Tp image data taken after the upgrade will automatically reflect this new algorithm, and Tr images reconstructed from Tp image data taken prior to the upgrade will have been reconstructed with the older version and properly stored as such. The images stored on a PACS will be the same as they were viewed by the radiologist or other health professional during the detection/diagnosis or other earlier review. Another advantage of the system of FIG. 2 is the reduced system reconstruction burden compared to the system in FIG. 1, where the reconstruction engine is just prior to the display. If there are multiple acquisition systems, for example four systems that are all pushing images to the display, then the reconstruction engine will need to reconstruct images at 4 times the rate of a reconstruction engine in a system having only one acquisition system, for the same total patient throughput.

An example of such a four-acquisition station system using the design of FIG. 1 is illustrated in FIG. 3. An example of a four-acquisition station system using the design of FIG. 2 is illustrated in FIG. 4, and this system can reconstruct more images in a given amount of time due to the increased number of reconstruction engines.

The question of which system design will place a greater burden on the PACS storage of an institution will depend upon the sizes of the raw projections Tp and of the reconstructed images Tr. In general, if the raw projections Tp are smaller than the reconstructed images Tr, it might be desirable to save in PACS the raw or preliminarily processed data for Tp images and reconstruct the final Tr images on demand for display or other use. In all cases it may be desirable to keep both of these sizes as small as possible.

One way to reduce the size of an original dataset for a Tp image is to bin the projection Tp data to as large a pixel size as practical without reducing clinical efficacy of the final Tp or Tr images. It can be particularly useful to bin the pixel data asymmetrically, with a coarser bin in the direction of motion of a source of the imaging x-rays relative to the breast being imaged and a finer bin in the orthogonal direction, as described in at least one of said earlier-filed patent applications. The binning can be done as a part of the X-ray data acquisition process, in the course of reading out measurement data from a flat panel digital imager. Alternatively, it can be done after initial data acquisition. Compression of the projections using lossless or lossy compression algorithms can also serve to reduce the image size. There are different known ways to reduce the size of the reconstructed datasets such as those for Tr images, and this can be particularly important if the reconstructions are being saved in PACS, and if they are being transmitted through the hospital or other facility network. Data compression is one way to reduce dataset size. Another is to make the reconstructed pixel sizes as large as practical consistent with the clinical imaging task. It is believed that, as one non-limiting example, a pixel size of 140 microns×140 microns for the reconstructed slices is reasonable for many if not most viewing purposes. The display system can interpolate or extrapolate along either or both the image directions to a finer pixel size for display, and this can be useful when it is desired to conform to the pixel size of another image, such as a digital mammogram taken at a finer resolution than 140 microns. It is also faster to reconstruct into a coarser pixel size in either or both image directions and then perform display interpolation or extrapolation to a finer pixel size, and doing so may not affect clinical efficacy as long as the reconstructed pixel size is adequately fine.

The tomosynthesis acquisition system can be dedicated to Tp image acquisition, or it can be capable of acquiring either mammograms Mp or tomosynthesis images Tp (reconstructed into tomosynthesis images Tr) in separate imaging sessions, or both in a single imaging session, as described in said earlier-filed applications. Thus, a display system preferably should be able to display both Mp and Tr (and/or Tp) images concurrently or sequentially or in toggled mode. Similarly, the display system preferably should be able to display the current images as well as additional images taken at other times. The tomosynthesis acquisition can acquire mammograms and tomosynthesis images Tp in a single compression, as described in said earlier-filed applications. In such a case, because the breast geometry is essentially unchanged between the two image types, a location in an Mp or Tr image can be related to the same breast location in the other image. If correlative geometry exists, the two image types can be overlaid on top of each other, and the user can toggle back and forth between which image type is visible at a given time. Thus, in general, the display can simultaneously or sequentially or in toggled mode display mammograms and tomosynthesis images Tr (and/or Tp) from the current and previous studies. Tr slices can be reconstructed all to the same size, which can be the same as the size of an Mp image of the breast, or they can be initially reconstructed to sizes determined by the fan shape of the x-ray beam used in the acquisition and later converted to that same size by appropriate interpolation/extrapolation.

Methods of identifying which image corresponds to which image type in displays of Mp, Tr and/or Tp images are desirable. One example of such a method is illustrated in FIG. 5. An icon is used to identify an image type. In this non-limiting example, the symbol M on the left image indicates that it is a mammogram. The symbol T on the right image indicates that it is a tomosynthesis slice image Tr. Similarly, a symbol Tp (not shown) can be used to indicate that the displayed image is a tomosynthesis projection image Tp, and the symbol 3D (also not shown) can be used to indicate that an image on the display is a 3D image. Other symbols/icons serving a similar purpose can be used instead of, or in addition, to those identified above. In the alternative, the images can be displayed without an identification of the type of image. For example, a Tr image and an Mp image can be displayed at the same time or toggled without displaying an indication of the type (Tr or Mp) of the image that is visible. This may be desirable in cases such as when a user has a familiar hanging protocol and does not need an express identification of the type of image.

The system described as a non-limiting example in this patent specification is capable of receiving and displaying selectively the tomosynthesis projection images Tp, the tomosynthesis reconstruction images Tr, and/or the mammogram images Mp, or a single type, or any subcombination of types. It can receive images stored uncompressed, losslessly compressed, and lossyly compressed. It can also include algorithms to decompress images sent in compressed format. The system has software to perform reconstruction of tomosynthesis image data for images Tp into images Tr. Further, it can include software to generate 3D display images from the tomosynthesis reconstructed images Tr using standard known methods such as MIP (Maximum Intensity Projection), summing, and/or weighted summing algorithms.

Referring to the tomosynthesis image Tr displayed on the right of FIG. 5, a slider bar indicates by means of a short horizontal bar the height of the displayed slice, in this example above the breast platform, although the height could be related to other references instead. In this case the height is approximately 5 cm, as seen from the marks 0, 2, 4, 6 (cm) on the vertical bar. The height of a Tr slice that is displayed can be changed using a standard computer interface, such as a keyboard or mouse or mouse wheel or trackball. When the height changes, the slider bar updates by moving up or down to accurately reflect the displayed slice. Another method of display is an overlay method, where the mammogram Mp and the tomographic slice image(s) Tr are stacked one on top of another. This is illustrated in FIG. 6. The symbol TM in this non-limiting example means that the display is an overlay of at least one tomosynthesis image Tr plus a mammogram image Mp. The visible image, that is the image type on top, can be changed from Tr to Mp and vice versa easily, such as toggling back and forth using a keyboard or another interface device. The image type that is visible can be identified by changing the symbols such as bolding or underlining the top one. For example, if the image Tr was on top, the symbol could be TM (T is foldface), while if the image Mp was on top the symbol could be TM (M is boldface). Alternatively, TM can be used when the Tr image is visible and MT when the Mp image is visible, or some other way can be used to show which image is on top and which is on the bottom of the display stack. As noted above, the top image can be made partly transparent, and other techniques such as fading one image into the other can be used. FIG. 6 further illustrates another display method. In addition to the slice height of a Tr image, the slice thickness can be adjusted and displayed, preferably non-numerically. In this example, the thickness of the horizontal bar that is between the marks for 5 cm and 6 cm indicates slice thickness scaled to the cm marks on the vertical scale. Alternatively, the displayed slice height and/or thickness can be displayed in a numeric format. Typically, the breast slices represented by Tr images are thin, on the order of 0.5-3 mm, and will not show objects that are far from the given slice. If it is desired to view objects seen from a thicker slice, one can perform reconstructions to generate Tr images of synthesized thicker slices, such as 5, 10, 15 or 20 mm or more, or two or more Tr images can be blended into a single Tr image representing a thicker slice. The blending can be with the same or different weighting of the original Tr images.

The selection of which Tr slice image should be displayed can be handled in a number of different ways. The user can click or drag the horizontal slider bar to the desired slice height, and the display would follow. Alternatively, the height could be selected using keyboard commands, mouse wheels or trackballs, or other such computer selection tools. The Tr slice image can be played in cine mode, with the speed and direction controllable by the user. Tomosynthesis projection images Tp can also be displayed in cine mode. If two sets of Tr images are displayed at the same time, for example a set from a current acquisition and a set from last year's acquisition for the same breast, it is possible that the thickness of the compressed breast changed, for example because the person's weight changed of because different compression was used. In such case, if each Tr image represents a breast slice of equal thickness, the number of images in one set may not be the same as that in the other. Several options are available for displaying the two sets concurrently in a scroll or cine mode. One is to move through the two sets at the same speed, in which case the end image of one set may remain on the screen while images from other set still change. Another is to move through the images at different speeds such that the end images of the two sets appear on the screen at the same time. Yet another is to change the images of one set (or both sets) such that the number of Tr images in each set is the same. This may involve interpolation/extrapolation that effectively changes the thickness of the slices in one or both sets, or omission of slices or repetition of the display of one or more slices. Similar synchronization or display mode selection is provided between scroll/cine displays of images for two breasts, As noted above, if two or more sets of tomosynthesis images are displayed concurrently, for example Tr images from the same breast taken at different times, or Tr images of the two breasts taken at the same time, these two sets of images can be simultaneously displayed in cine mode. The cine displays can be synchronized, so that if these two datasets represent the same breast, the cine display of both will traverse through each breast dataset at the same rate.

The display of the slice image Tr has, in addition to the display of the slice height, a graphical method of displaying the corresponding slice thickness. The width of the cross-bar shown in FIG. 6 illustrates the slice thickness.

These Tr images for thicker slices can be derived in several ways. One way is to sum together a number of the adjacent thinner Tr slice images. Another is to calculate a maximum intensity projection through the adjacent slices. Yet another way to change the slice thickness is to reconstruct the dataset using a subset of the projections Tp. If one uses fewer projections, this is equivalent to an acquisition over a shallower angle and consequently the reconstructed images Tr have a greater depth of field and thus represent thicker slices. For example, if only one projection is used to reconstruct, this represents a tomosynthesis acquisition over a 0° angular scan and the depth of field is infinite, i.e. the reconstructions are 2D, as in an Mp image of the same breast.

In the most general case, the display screens will contain a mixture of mammogram Mp, tomosynthesis Tr and/or Tp, and combination (Mp+Tp/Tr) images. One example of this is illustrated in FIG. 7. It shows a 4-view examination being compared to a prior 4-view exam, where different views of different breasts are either Mp, Tr/Tp, or combination displays. The software allows the selection of one or more image planes, for use in image processing, or to change window/level or to change slice height, etc. The selected image planes are indicated in this case in some way; in this non-limiting example the selected plane is outlined with a dotted line. These sets of images can be on one monitor, or on multiple monitors or other displays. In the alternative, one or more or all of the displayed images can be shown without an identification of the type of image, e.g., without notation such as TM or M When more than one image is displayed, it can be convenient to have the images all be displayed at the same pixel spacing, using known interpolation or extrapolation methods applied to digital images. This can facilitate image comparison. As an example, if the prior mammogram was acquired on a system using 100 micron pixel spacing, but the current mammogram was acquired on a system using 70 micron pixel spacing, the display can map the images so the pixel spacings are identical. This pixel spacing adjustment can also be used for Mp and Tr/Tp images. In a preferred embodiment, the Mp and Tr/Tp images are displayed at the same pixel size. This is especially useful in performing overlaid or toggled image display, with the Mp and Tr/Tp images on top of each other. Thus, an object in a Tr image will appear at the same place as in the corresponding Mp image. If the two images arc not at the same pixel size, toggling between them may show a distracting change due to the difference in pixel size. Matching the pixel spacings for all images on the display is only one possibility. A capability to change the pixel spacings of any image or sets of images, such as would occur when one zoomed a region of a breast, can also be included.

Zooming can be done on any of the images on the display. For example, in a combo overlay display mode, the zoomed area will zoom both the Mp and the Tr slice images as they are toggled. In other words, no matter what image type is displayed, it will be zoomed. Window/level can be independently, or jointly, applied to any combination of images on the display. In particular, for the Tr images the window/level can be applied to just the single displayed Tr slice image, or all the Tr slice images. If there is a magnified region of an image, window/level can be selectively applied just to the magnified region or to the entire image.

A compressed breast is frequently about 50 mm thick, and if the reconstructed slice pitch or separation is 1 mm then the examination will consist of 50 slices. The time it takes to load this study into display might be significant. Because of this, it can be useful for the display to indicate the status of the display if the image is currently being loaded. This can take the form of a message such as "image loading" or an icon indicating the same, or information providing more detail regarding loading status such as, without limitation, remaining time for completed display.

The sequence of displaying Tr images can be controlled to select either the first, last, or middle, or some other Tr slice image, as the initial slice to display. This control also defines the starting slice thickness to display.

CAD algorithms are commonly used to analyze mammograms. CAD can also be applied to Tr and/or Tr images. It can be useful to display CAD marks that are derived from or are otherwise associated with the Tr/Tp images, at or for the appropriate locations on the Mp images. For example, when a Tr slice image is displayed that contains one or more CAD marks, the x,y location of the CAD mark on the Tr slice image is used to compute the corresponding x,y location on the Mp image that represents the same breast location. The mark can then be placed on one or both of the Mp and Tr images at the same locations. Similarly, it can be useful to display CAD marks that are derived from or are otherwise associated with the Mp images on the appropriate locations on the Tr slice images. For example, the x,y location from the Mp CAD mark is used to compute the corresponding x,y location on the Tr slice image that represents the same breast location, and the mark is placed on the Tr slice.

One method of displaying CAD information is illustrated in FIG. 8. Slice locations where there are CAD marks are indicated. In this example, they are indicated though the use of arrows positioned at the slice heights where the marks are. In this non-limiting example, there were CAD marks at heights 1 and 3 cm, and the currently displayed slice is at 5 cm.

Another display method for use with Tr images that have Tr CAD data is to restrict the display of Tr slice images that do not have CAD marks on them. For example, if only Tr slice images 10 and 20 had CAD marks, then only those two slice images would be displayed. This allows the speedup of image review, because there can be 50 or more Tr slices that need to be displayed. The image display could jump from one CAD-marked slice image Tr to another quickly. There can also be an override method so that all the slice images Tr could be reviewed if desired.

In addition to CAD information display, the unit can display patient demographic and acquisition information relevant to the acquisition and reconstruction of Tp/Tr images.

There also are different methods of printing Tr/Tp images. Because there are many slice images Tr, it may not be desirable to print out each individual slice image on separate sheets. In this case, the system can support printing of the Tr images in an N×M film layout format. In addition, printing can be allowed in a screen capture WYSIWYG (What You See Is What You Get) format, or for only selected ones of the images, for example images that have CAD marks associated with them.

A common method of reviewing digital mammography and tomosynthesis images Mp, Tp, and Tr is by using one or more monitors, and looking at the images in an essentially monoscopic mode—the same image is viewed by both of the viewer's eyes. Researchers have proposed using stereo viewing systems, whereby different images are presented to the left and right eyes. This method of viewing is known as stereoscopic, and can offer distance or depth cues similarly to what is normally seen by human eyes in regular vision tasks. Stereoscopic viewing offers potential benefits in viewing radiological images, because relative spatial relationships between objects in the body might be more apparent. One such stereoscopic system, for use in medical displays, is proposed in U.S. Pat. No. 6,031,565 issued on Feb. 29, 2000 and involves taking two radiographic images of a body from different angles. The display of these two images provides depth information.

Tomosynthesis images offer new opportunities for improved stereoscopic viewing, at least in part because it provides a richer dataset than just a stereo pair to be displayed, it provides many possible combinations of image pairs, and provides for scrolling through different displayed sets of images.

One method of display using pairs of images from the tomographic projection dataset Tp is illustrates in FIG. 9. Any two pairs of projections Tp may provide stereo visualization, and by displaying dynamically sets of these pairs of projections, one will get both a stereoscopic view and one which dynamically moves around the body that was imaged. For example, consider that 8 projections Tp were taken as a part of a tomosynthesis acquisition: Tp[1], Tp[2], . . . Tp[21]. The first pair to be stereo viewed could be Tp[1] and Tp[3], the second pair Tp[2] and Tp[4], the third pair Tp[3] and Tp[5] and so on to Tp[6] and Tp[8]. Alternatively pairs could be adjacent pairs such as Tp[1] and Tp[2] or separated by three projections Tp[1] and Tp[4], etc. The optimal spacing between the two projections in the displayed stereo pair is dependent upon the imaging geometry and angular separation between successive projections Tp[i] and Tp[i+1]. It is known that only certain angular differences between stereo pairs give good stereo visualization to humans, and the selection of appropriate pairs of images Tp for a particular acquisition setting can be determined through convenient experimentation.

Another method of display uses a variant of the reconstructed dataset Tr and is illustrated in FIG. 10. In this embodiment, one reconstructs two different datasets Tr' and Tr", both reconstructed from some or all of the original projections Tp. When performing reconstruction, one chooses the geometry of reconstruction and it is possible to reconstruct these two datasets into images Tr that differ in their view of the body by a selected angular separation, e.g. a few degrees, thus mimicking the apparent viewing of the body that the human eye would see, if it had x-ray vision. Each dataset Tr' and Tr" consist of sets of cross sectional slices. If one displays, using the stereo viewer, the same slice from Tr' and Tr", one in the left eye and the other in the right eye, one would get a stereo perspective of that slice. One could display different slice pairs in depth succession in the breast to get a dynamic stereo view through the body. As seen in FIG. 9, an object 3000 is reconstructed with cross-sectional slices Tr' and Tr" perpendicular to two different axes 3001 and 3002. The slice pairs that are displayed to the left and right eye are Tr'[i] (3003) and Tr"[i] (3004). The angle between 3001 and 3002 is such that viewing the pairs Tr' and Tr" gives a stereoscopic visualization. Unlike the proposal in said U.S. Pat. No. 6,031,565, FIG. 9 illustrates a stereo view of a thin cross-sectional slice through the body, and a scroll through such sections, while the patent proposes displaying stereo pairs of projection radiographs through the entire body.

FIG. 11 illustrates an overall mammography/tomography system in which the preferred but non-limiting examples discussed above can be implemented. The Figure illustrates in block diagram form an x-ray data acquisition unit 100 that includes an x-ray source 110 imaging a breast 112 supported on a breast platform 114. An x-ray imager 116 such as a flat panel x-ray imager commercially available from the assignee of this patent specification generates projection image data that can be a mammogram Mp or a tomosynthesis projection image Tp. X-ray source 110 is mounted for movement around breast platform 114 so that images Tp can be taken at different angles. X-ray imager 116 can be stationary or it can also move relative to breast platform 114, preferably in synchronism with movement of x-ray source 110. Elements 110 and 116 communicate with x-ray data acquisition control 118 that controls operations in a manner known from said earlier-filed patent specifications. X-ray image data from imager 116 is delivered to processing and image reconstruction unit 120, where the data is processed as known from said earlier-filed patent application into Tp and Tr image data, possibly stored, and prepared for display at image display unit 122 as disclosed in the various embodiments described above. The appropriate software to carry out the processes describe above can be written by programmers skilled in the art based on the disclosure above and general knowledge in the art without due experimentation, and in general will be different for different data processing platforms.

Figure 12:
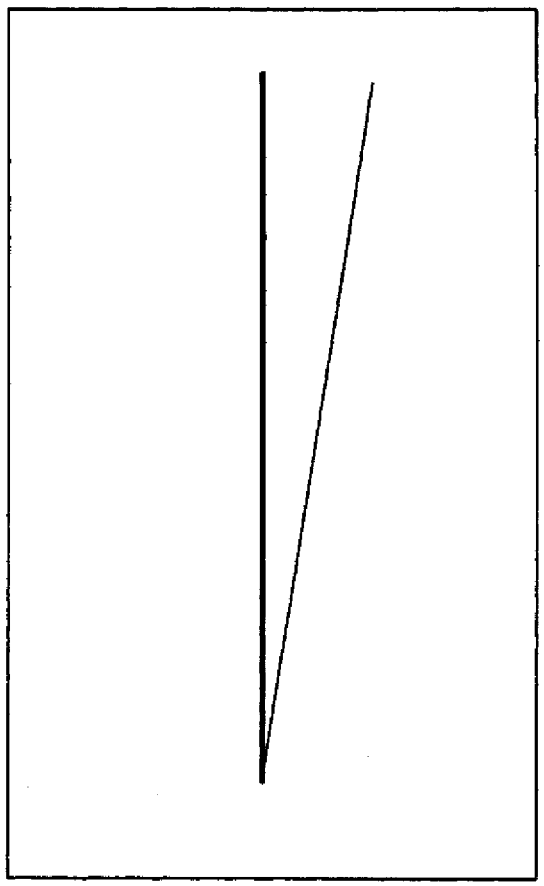
FIG. 12 illustrates an example of a non-numeric display indicative of the angle of a slice represented by a Tp image relative to a frame of reference such as the breast platform.

FIG. 12 illustrates a non-numeric way of indicating the orientation of breast slices that are represented by Tp images. In this example, the thicker vertical line indicates a direction normal to the breast platform on which the compressed breast rests for the Tp image and the thinner line indicates the orientation of a slice represented by a Tp image (not shown in FIG. 12) that is being displayed.

The examples described above are only illustrative and that other examples also are encompassed within the scope of the appended claims. It should also be clear that, as noted above, techniques from known image processing and display methods such as post-production of TV images and picture manipulation by software such as Photoshop from Adobe, can be used to implement details of the processes described above. The above specific embodiments are illustrative, and many variations can be introduced on these embodiments without departing from the spirit of the disclosure or from the scope of the appended claims. For example, elements and/or features of different illustrative embodiments may be combined with each other and/or substituted for each other within the scope of this disclosure and appended claims.

The invention claimed is:

1. A tomosynthesis system comprising:
an x-ray source selectively emitting an imaging x-ray beam, a breast immobilizing structure defining a volume for a patient's breast, and an x-ray imaging receptor arranged such that said x-ray beam passes first through the volume for the patient's breast before impinging on the imaging receptor;
a source support mounting the x-ray source for selective movement relative to the breast immobilizing structure;
an x-ray data acquisition control configured to:
cause the x-ray source to move through a plurality of different imaging positions relative to the breast immobilizing structure and selectively illuminate the imaging receptor with the x-ray beam for each of the imaging positions, and
cause the imaging receptor to provide imaging data in response to being illuminated with the x-ray beam for the different imaging positions;
a processing and image reconstruction unit configured to receive and process the imaging data and generate a plurality of projection x-ray images Tp and a plurality of reconstructed slices images Tr, wherein:
each image Tp is a projection x-ray image of the volume for the patient's breast taken with the x-ray beam for a respective one of the plurality of different positions of the x-ray source relative to the breast immobilizing structure; and
each image Tr is an image of a respective 3-dimensional slice of the volume for the patient's breast reconstructed through computer processing using at least several of the projection images Tp; and
an image display unit configured to selectively display selected ones of the slice images Tr and projection images Tp concurrently with indicia identifying each displayed image as a projection or a slice image.

2. The system of claim 1 in which the image display unit is further configured to display, concurrently with the display of a slice image Tr, indicia identifying a position of a respective 3-dimensional slice occupies in the volume for the patient's breast.

3. The system of claim 2 in which the display unit is further configured to show the position of slice by a mark on a bar, and to respond to user input moving the mark relative to the bar to change from one displayed Tr image to another.

4. The system of claim 1 in which the processing and image reconstruction unit is further configured to apply computer aided detection (CAD) processing to at least one of the Tp and Tr images to thereby identify suspected abnormalities therein, and the image display unit is configured to selectively display CAD marks on at least one of the displayed images identifying the locations therein of the suspected abnormalities.

5. The system of claim 1 including an anti-scatter grid between the volume for the patient's breast and the imaging receptor.

6. The system of claim 5 in which the grid comprises x-ray attenuating partitions that are focused on the x-ray source in at least one dimension.

7. The system of claim 6 in which the grid partitions are focused on the x-ray source in two dimensions.

8. The system of claim 1 in which the imaging receptor moves relative to the volume for the patient's breast while the x-ray source moves through the imaging positions.

9. The system of claim 1 in which the processing and reconstruction unit is configured to generate a mammogram image, and the image display unit is configured to display the mammogram image concurrently with the display of at least one of the Tp and Tr images.

10. The system of claim 1 in which the display unit is configured to concurrently display two or more images Tp that are taken for imaging positions separated from each other by at least one other imaging position.

11. The system of claim 1 in which the display unit is configured to concurrently display two or more images Tr that represent slices oriented to conform to intersecting planes.

12. A method comprising:
moving an x-ray source through a plurality of different imaging positions relative to a breast immobilizing structure and selectively illuminating the immobilizing structure and then an imaging receptor with the x-ray beam for each of the imaging positions;
deriving imaging data from the imaging receptor in response to being illuminated with the x-ray beam for said different imaging positions;
computer-processing the imaging data to generate projection x-ray images Tp and a plurality of reconstructed slices images Tr, wherein:
each image Tp is a projection x-ray image of the volume for the patient's breast taken with the x-ray beam for a respective one of the different positions of the x-ray source relative to the breast immobilizing structure; and
each image Tr is an image of a respective 3-dimensional slice of the volume for the patient's breast reconstructed through computer processing using at least several of the projection images Tp; and
selectively displaying selected ones of the slice images Tr and projection images Tp concurrently with indicia identifying each displayed image as a projection or a slice image.

13. The method of claim 12 including displaying, concurrently with the display of a slice image Tr, indicia identifying a position of a respective 3-dimensional slice in the volume for the patient's breast.

14. The method of claim 13 including showing the indicia as a mark on a bar, and responding to user input moving the mark relative to the bar to change from one displayed Tr image to another.

15. The method of claim 12 applying computer aided detection (CAD) processing to one or more of the Tp and Tr images to thereby identify suspected abnormalities therein, and selectively displaying CAD marks on one or more of the displayed images to identify the locations therein of the suspected abnormalities.

16. The method of claim 12 including providing an anti-scatter grid between the volume for the patient's breast and the imaging receptor.

17. The method of claim 16 including focusing the grid on the x-ray source in at least one dimension.

18. The method of claim 17 including focusing the grid on the x-ray source in two dimensions.

19. The method of claim 12 including moving the imaging receptor relative to the volume for the patient's breast while moving the x-ray source through the imaging positions.

20. The method of claim 12 generating a mammogram image and displaying the mammogram image concurrently with the display of one or more of the Tp and Tr images.

21. The method of claim 12 including concurrently displaying two or more images Tp that are taken for imaging positions separated from each other by at least one other imaging position.

22. The method of claim 12 including concurrently displaying two or more images Tr that represent slices oriented to conform to intersecting planes.

23. A method comprising:
moving an x-ray source through a plurality of different imaging positions relative to a breast immobilizing structure and selectively illuminating the immobilizing structure and then an imaging receptor with the x-ray beam for each of the imaging positions;
deriving imaging data from the imaging receptor in response to being illuminated with the x-ray beam for said different imaging positions;
computer-processing the imaging data to generate projection x-ray images Tp and a plurality of reconstructed slices images Tr, wherein:
each image Tp is a projection x-ray image of the volume for the patient's breast taken with the x-ray beam for a respective one of the different positions of the x-ray source relative to the breast immobilizing structure; and
each image Tr is an image of a respective 3-dimensional slice of the volume for the patient's breast reconstructed through computer processing using at least several of the projection images Tp; and
concurrently displaying two or more images, of which at least one is a slice image Tr and at least one is a projection image Tp.

* * * * *